US006309346B1

United States Patent
Farhadi

(10) Patent No.: US 6,309,346 B1
(45) Date of Patent: Oct. 30, 2001

(54) CREEPING COLONOSCOPE

(76) Inventor: Ashkan Farhadi, Ashkan Farhadi Medical Office Gharan Street, Sari 48186 (IR)

( * ) Notice: Subject to any disclaimer, the term of this patent is extended or adjusted under 35 U.S.C. 154(b) by 0 days.

(21) Appl. No.: 09/605,826

(22) Filed: Jun. 29, 2000

(51) Int. Cl.$^7$ ....................................... A61B 1/01
(52) U.S. Cl. ........................................ 600/114; 604/95.01
(58) Field of Search .................................... 600/114, 101; 604/95.01, 95.03; 356/241.1

(56) References Cited

U.S. PATENT DOCUMENTS

| | | | |
|---|---|---|---|
| 5,906,591 | * | 5/1999 | Dario et al. ........................... 600/114 |
| 6,162,171 | * | 12/2000 | Ng et al. ................................ 600/114 |

* cited by examiner

Primary Examiner—John Mulcahy

(57) ABSTRACT

Improving upon conventional endoscope patent, the proposed design (Creeping colonoscope) has a new mechanism for movement of the conventional colonoscope in the large intestine. This method of movement, which resembles climbing a ladder, where hands could assist the climbing force of the feet results from consecutive appliance of a pair of sucking arms on the tip of the colonoscope to the adjacent mucosa. The sucking arms adhere to the mucosa by vacuum power provided by an external suction device and pull the mucosa toward the tip of the fiberoptic colonoscope after mucosal adhesion. Successive repetition of this operation not only pulls the mucosa over the colonoscope but also moves the colonoscope tip onward. It should be noted that this mechanism of action is not a substitute of the primary mode of movement of the colonoscope induced by pushing of the shaft. But this minor movement help the colonoscope to pass the flexures more smoothly and with less pushing force that induce pain and discomfort for the patients. Passing the tip beyond the flexure, the endoscopist would be able to perform hooking and shortening (straightening) maneuver more easily and this leads to better transmitting of the pushing force to the tip of the colonoscope. The result is less effort and procedure time on the physicians' end and less pain and discomfort on the patients' end.

20 Claims, 5 Drawing Sheets

CREEPING COLONOSCOPE

STATEMENT REGARDING FEDERALLY SPONSORED RESEARCH OR DEVELOPMENT

Not applicable.

REFERENCE TO MICROFICHE APPENDIX

Not applicable

BACKGROUND OF INVENTION

As is known endoscopic technique was developed in the medical field with the aim to improve the evaluation of the human hollow cavities. Gastrointestinal tract was one of the first places that were captured by endoscopic procedures. Prior art in this field includes the design of endoscope, a well-known optical system that was disclosed and claimed in U.S. Pat. No. 3,449,037 issued to C. J. Koester on June 1969. Currently used fiberoptic endoscopes are comprised of many lenses mounted in a flexible tube to relay an image from inside a body cavity for viewing by a physicians for diagnosis or manipulation inside those cavitary spaces. Colonoscope is one of these instruments that can be used to investigate the large bowel. Colonoscope is pushed inside the colon through anal canal. As long as this instrument moves straight, the friction force is trivial and nearly all the forward pushing force transmits through the shaft to the tip of the colonoscope and this force moves the tip of the colonoscope to ward the front (FIG. 1, drawing sheet 1). However the human colon is not a straight conduit and passing bends or flexures of the colon, will stretch the colon over the passing fiberscope and this will result in large friction and shearing forces that would resist onward movement of the fiberscope. At this stage the pushing force over the shaft of colonoscope, has to overcome the friction and shearing forces to move the tip ahead (FIGS. 2,3, Drawing sheet 1). On the other hand stretches of the flexures bring about discomfort and pain for the patient during the procedures. Passing more flexures during the procedure produce more friction and shearing forces, up to the point that colonoscope can no longer be pushed forward despite great pushing effort and pushing the tube will only result in producing a loop in more redundant portion of the colon such as sigmoid or transverse colon which brought-more pain and discomfort for the patient.

There are several colonoscopic maneuvers that have been proposed to overcome this problem. These maneuvers try to bring the colonoscope in to a straight position by hooking the tip of the colonoscope (FIG. 4, drawing sheet 1) and shortening (straightening) of the colonoscope (FIG. 5, drawing sheet 1). These maneuvers decrease the bends and flexures by aligning them in a nearly rectilinear position to reduce the friction and shearing forces (FIG. 6, drawing sheet 1) and this leads to better transmitting of the pushing force to the tip of the colonoscope.

The idea of creating this device dawned on me during a burdensome colonoscopic procedure. The colonoscope was stuck in the hepatic flexure of a 60-year-old man suspicious of having a cecal tumor who had a redundant, tortuous colon. Meanwhile I was in absolute despair of accomplishing a pancolonoscopy, I tried to pull the mucosa toward the fiberoptic colonoscope by grasping the distant bowel mucosa by biopsy forceps. After several attempts (and several untoward mucosal biopsy takings), the colonoscope moved just a bit forward and this enabled me to hook the tip of the colonoscope over the flexure and short the colonoscope to bring it in to a straight position. Eventually a successful pancolonoscopy was performed in that case. Although using biopsy forceps for pulling the colonoscope onward might be useful in some circumstances, but the grasped mucosa usually returns to its previous position as soon as it become released. The other problem is the obscuring of the luminal view by the mucosa approaching the colonoscope.

Initially I proposed a simple method for pulling the colonoscope forward. In this method I used two plastic flexible tubes which were secured along the side of the conventional colonoscope by its full length by an ordinary bonding strip. These tubes make it possible to transfer two biopsy forceps simultaneously to the tip of the colonoscope and grasp the mucosa successively to prevent reverting of the mucosa after releasing. The major problem of this simple device was multiple untoward mucosal biopsy takings, making several mucosal artifacts that might be mistaken for mucosal lesion.

Creeping colonoscope applies the same mechanism for moving ahead but lacks those disadvantages by replacing sucking arms instead of biopsy forceps. This resembles climbing a ladder, where hands could assist the climbing force of the feet. The sucking arms adhere to the mucosa by sucking pads and would pull the mucosa toward the tip of the fiberoptic colonoscope. Successive repetition of this operation not only pulls the mucosa over the colonoscope but also moves the colonoscope tip toward the front. This provides a great improve t of the movement of the conventional colonoscope in the colon.

The mechanism for movement of the new colonoscope that I have designed has some similarities to the endoscopic robot by Dario P et. al. In patent U.S. Pat. No. 5,906,591 on May 1999. The endoscopic robot designed for being inserted in to a body cavity of a patient and advanced therein in a prefixed direction with a so called inch-worm like motion, comprising a variable length segment and aspiration means for selectively producing a pneumatic vacuum between robot and the body cavity wall, allowing the inch-worm like motion avoiding, at the same time any pushing action against the body cavity. But there are several major differences in the design of the endoscopic robot and creeping colonoscope:

1. Endoscopic robot is a robot that can be controlled from out side of the body and it is equipped with servomotor microarms, microcameras and laser emitter for diagnostic and possible therapeutic maneuvers. But creeping colonoscope composed of a conventional colonoscope (fiberscope) with a new improved mechanism of movement 2. The major force of the movement of the endoscopic robot is provided by its inch-worm movement independent of any external pushing force, while the creeping colonoscope is mainly dependant on external pushing force for its movement. Actually the pulling force is designed to be used only when the colonoscope is passing the flexures or stucked in the colon because of looping of the colonoscope in redundant portion of the sigmoid and transverse colon.

3. The mechanism of action of the endoscopic robot is inchworm-like motion. It means that it has a proximal and distal part that can selectively adhere to the bowel mucosa by applying the vacuum. The intermediate portion is flexible and results in movement of the instrument during successive appliance of the proximal and distal vacuum adherence. The mechanism of the action of the creeping colonoscope composed of protruding and retracting of a pair of effectors that are mounted on the side wall of colonoscope tip. Each effector composed of an arm that is able to protrude forward in to the lumen after the release by a spring force, adhering to the mucosa via their sucking pad by vacuum power which would be applied after the protrusion, result in withdrawal of the sucking arm in to its initial position. Pulling forces would be generated by withdrawal of the protruded arm that will be adhered to the bowel mucosa and successive alternative appliance of a pair of these arms to the adjacent mucosa would be able to propel the colonoscope a few centimeters forward enough to pass the flexures. Although both instrument move by successive appliance of the vacuum to the mucosa, there are a great differences in the mode of vacuum appliance (fixed proximal and distal portion with flexible middle part versus retracting side arm appliance) and mode of movement (inchworm movement versus ladder climbing using alternate hands) in these two instrument and the only similarity is the using pneumatic vacuum for movement.

The other device that has been designed for advancing an endoscope through a body passage was invented by Meiri, Through patent number U.S. Pat. No. 4,207,872, on June 1980. This instrument composed of a sleeve having an annular chamber defined in part by an outer wall of elastometeric material. A multiplicity of resilient hollow protrusions are formed in the wall and expand outwardly and rearwardly when the chamber is filled with a suitable fluid under pressure and which retract inwardly and forwardly when the pressure of the fluid is reduced. This device is secured to the distal end of endoscope and by repetitious expansion and retraction of the protrusion, such device would move forward. There are several differences between this invention and creeping colonoscope:

1. This device moves forward by pushing force of the expanded projections, while creeping colonoscope move forward by pulling force of the sucking arms.
2. The colonic mucosa is elastic and easily could be pulled or pushed (high compliance). This characteristic of the colon will produce a great difficulty for the designed device to move in the colon. Therefore when the projections push the colonic wall backward to move the endoscope forward, they only move the colonic wall backward and after retraction of the projections the colonic wall return to its place. If the colonic wall were more rigid this instrument would move the endoscope forward. The creeping colonoscope use the sucking arm which adhere to the mucosa and pull it and keep it in this position till the second arm applied to the mucosa and pull the mucosa again. This action would be repeated successively by the pair of the arms. Repetition of this action will stretch the mucosa to the point that moving of the colonoscope forward is easier than moving the mucosa backward. In this situation the elastic force of the colonic wall would be reached or exceed the force that is needed to move the tip of the colonoscope onward.
3. Adhering of the tip of the colonoscope to the mucosa by sucking arms secures the position of the colonoscope in the colon and enable the endoscopist to perform the hooking and shortening (straightening) maneuvers easily. This possibility is not provided by the proposed design.

LeVeen invented another design of the similar instrument, which uses pneumatic bellows for generating pushing force to move a catheter inside a hollow cavity, through patent number of U.S. Pat. No. 4,389,208, on June 1983. This catheter advancer has similar mechanism of movement as was described for previous invention designed by Meiri, but the differences are presence of bellows rather than expanding projections and the propelled device is a catheter rather than an endoscope.

The other device in this field designed by Choy, with patent number of U.S. Pat. No. 3,895,637, on July 1975. This invention which has a complex design composed of multiple balloons and membranes for securing the endoscope in the lumen of the intestine and propel the device by inflating of the other balloons. This self propelled conduit-traversing device also use pushing force of the inflated balloons.

The other device that has been invented to move the long instrument inside the intestinal lumen was proposed by Krasner through patent number U.S. Pat. No. 4,676,228, on June 1987. This medical apparatus having inflatable cuffs and a middle expandable section and the mechanism of the movement is using multiple balloons (cuffs) and a portion that could be extended after securing of the balloons in the lumen.

There is another instrument that proposed to perform endoscopic procedure by robot. Robotic endoscopy was invented by Grudfest with the patent number U.S. Pat. No. 5,337,732, on August 1994. These device moves in the body cavity by a mechanism resemble inchworm or snake. A balloon fixes the robot tail inside the lumen after inflation. The extendable head then can move forward and then could be secured inside the lumen by another balloon till the tail retract the reach the head. This repetition of the inflating and deflating balloons and moving multiple segments moves the robot inside of the body cavity. This robot is also provided with microcamera and multiple arms to perform diagnostic or therapeutic procedures.

Other apparatus that is invented for endoscopic examination designed to move an endoscope by transmitting burst of energy wave (radiofrequency or ultrasonic) to the end of the endoscope and provide inflation of the balloons for movement of the endoscope. Frazer through U.S. Pat. No. 4,176,662 invented this device, on December 1979.

Other lumen-traversing ice was invented by Oritz with patent number U.S. Pat. No. 5,398,670, on March 1995. This instrument also uses three balloons and a moveable middle portion. Another insertion assisting device for medical instrument was designed by Kruger, through patent number U.S. Pat. No. 5,454,364, on October 1995. This instrument uses inflatable chamber, which push the intestinal wall to move the endoscope with the inertia force of the pushed wall.

BRIEF SUMMARY OF THE INVENTION

Improving upon conventional endoscope patent, the proposed outline claims a new design of colonoscope that improve the mechanism for movement of the conventional colonoscope in to large intestine. This method of movement, which resembles climbing a ladder, where hands could assist the climbing force of the feet, results from consecutive appliance of a pair of sucking arms to the adjacent mucosa. The pair of the sucking arms are part of the effectors that are mounted of the side wall of the conventional fiberoptic colonoscope. Each effector composed of an extenal tube which fixed to the side wall of the tip of the colonoscope and an internal tube (sucking arm) that can move inside the external tube. The outward movement of the internal tube is provided by a coil spring force and the withdrawal is provided by the vacuum power after adherence of the sucking arm to the colonic mucosa. Withdrawal of the adhered sucking arms move the mucosa toward the tip of the fiberoptic colonoscope. Successive alternative repetition of this operation by the right and left sucking arms not only pull the mucosa over the colonoscope but also move the colonoscope tip onward. The controle of the effectors is performed by controlers which are mounted on the controling panel of the conventional colonoscope. There are one pair of controlers that regulate the operation of the effectors through the connecting components. The controlers controle the release, adherence (applying the vaccume power) and withdrawal of the sucking arms in each side seperately. There is a pair of connecting parts that connect the controlers to the effectors. These parts not only transmit the vaccume power from controlers to the effectors but also transmit the releasing wires which control the releasing of the effectors. The suction tubes, which composed of a simple tubes, connect the controlers to the external suction device and transmit the vaccume power to the controlers.

It should be noted that this mechanism of action is not a substitute of the primary mode of movement of the colonoscope induced by pushing of the shaft. But this minor movement help the colonoscope to pass the flexures more smoothly and with less pushing force that induce pain and discomfort for the patients. Passing the tip beyond the flexures, the endoscopist would be able to perform hooking and shortening (straightening) maneuver more easily and this maneuver leads to better transmitting of the pushing force to the tip of the colonoscope. The result is less effort and procedure time on the physicians' end and less pain and discomfort on the patients' end.

BRIEF DESCRIPTION OF THE SEVERAL VIEWS OF THE DRAWING

Drawing Sheet 1

Drawing Sheet 2

Figure 1:
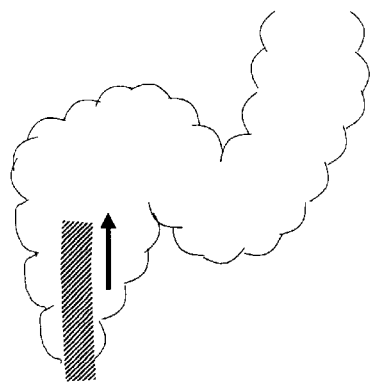
FIG. 1: Colonoscope entered the colon. It moves easily until reaching the flexures.
Figure 2:
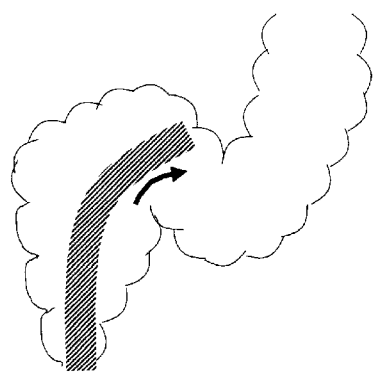
FIG. 2: passing a flexure increases the shearing force and need more pushing force for moving.
Figure 3:
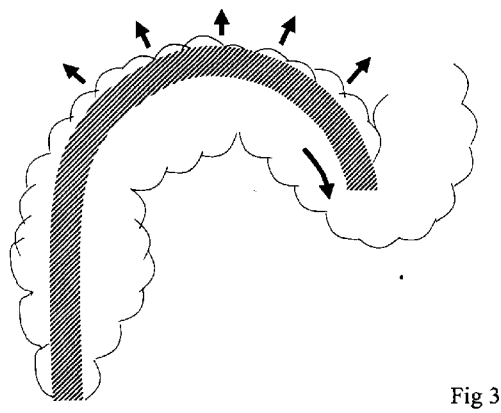
FIG. 3: Passing more flexures changes the alliance of the direction of the pushing force to the direction of the movement of the tip of the colonoscope. This result in the streching of the bowel and increase tesion in the colon wall which brought pain and discomfort for the patient. This stage is the initiation of the loop formation.
Figure 4:
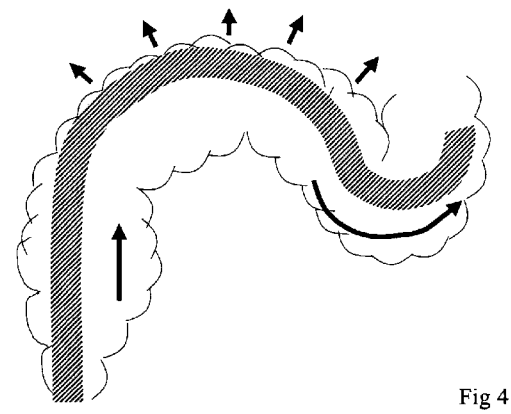
FIG. 4: The angle of the pushing force on the shaft reached to a stage that pushing more can even result in backward movement of the tip of the colonoscope. In this stage the loop is formed and pushing of the colonoscope stretches more the bowel wall especially in the redundant portion of the colon (sigmoid or transverse) and the only result is pain and discomfort for the patient.
Figure 5:
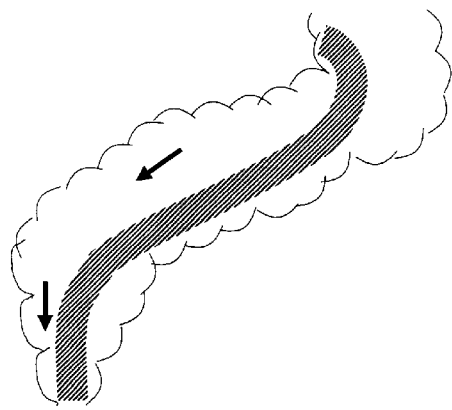
FIG. 5: Hooking of the tip of the colonoscope beyond a flexure and shortening (straightening) of the colonoscope.
Figure 6:
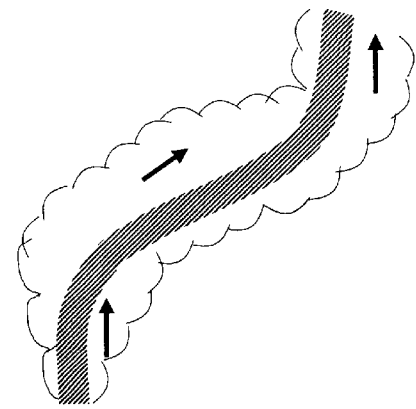
FIG. 6: Straightening of the colonoscope, it could be pushed forward again.
Figure 7:
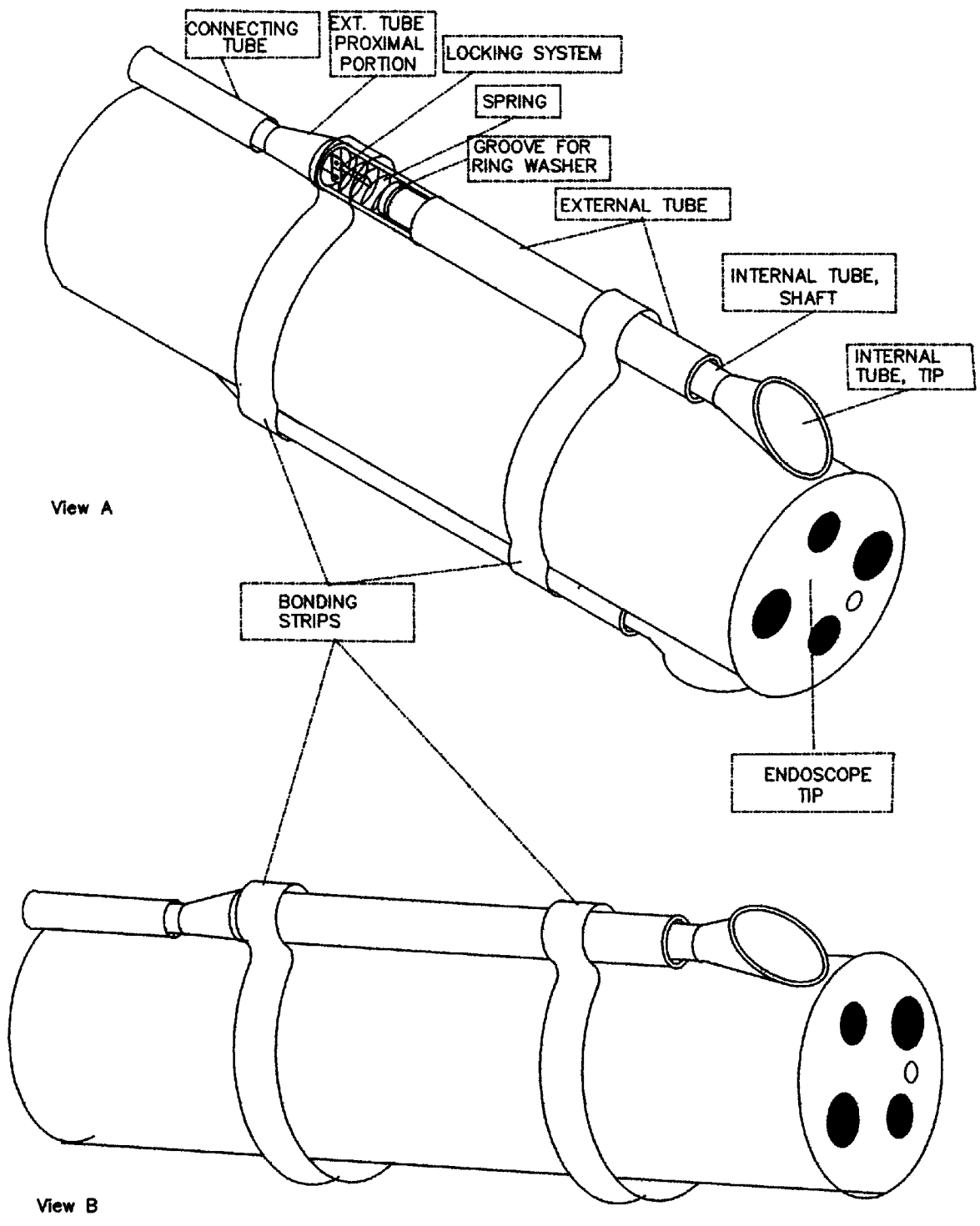

FIG. 7 is a model of the creeping endoscope. In this FIG. 2 three dimensional view of the tip of the colonoscope is seen. A pair of the effectors are seen on each side of the colonoscope tip. The external tubes are fixed to the side wall of the of the colonoscope by bonding strips. The internal tubes (sucking arms) with their obtuse angel, funnel shaped sucking pad are seen inside of the external tubes. The proximal part of the external tube is exposed for better visualization of the coil spring position and locking system. The connecting tube and connecting wire are attached to the proximal end of the external tubes.

Drawing Sheet 3

Figure 8:
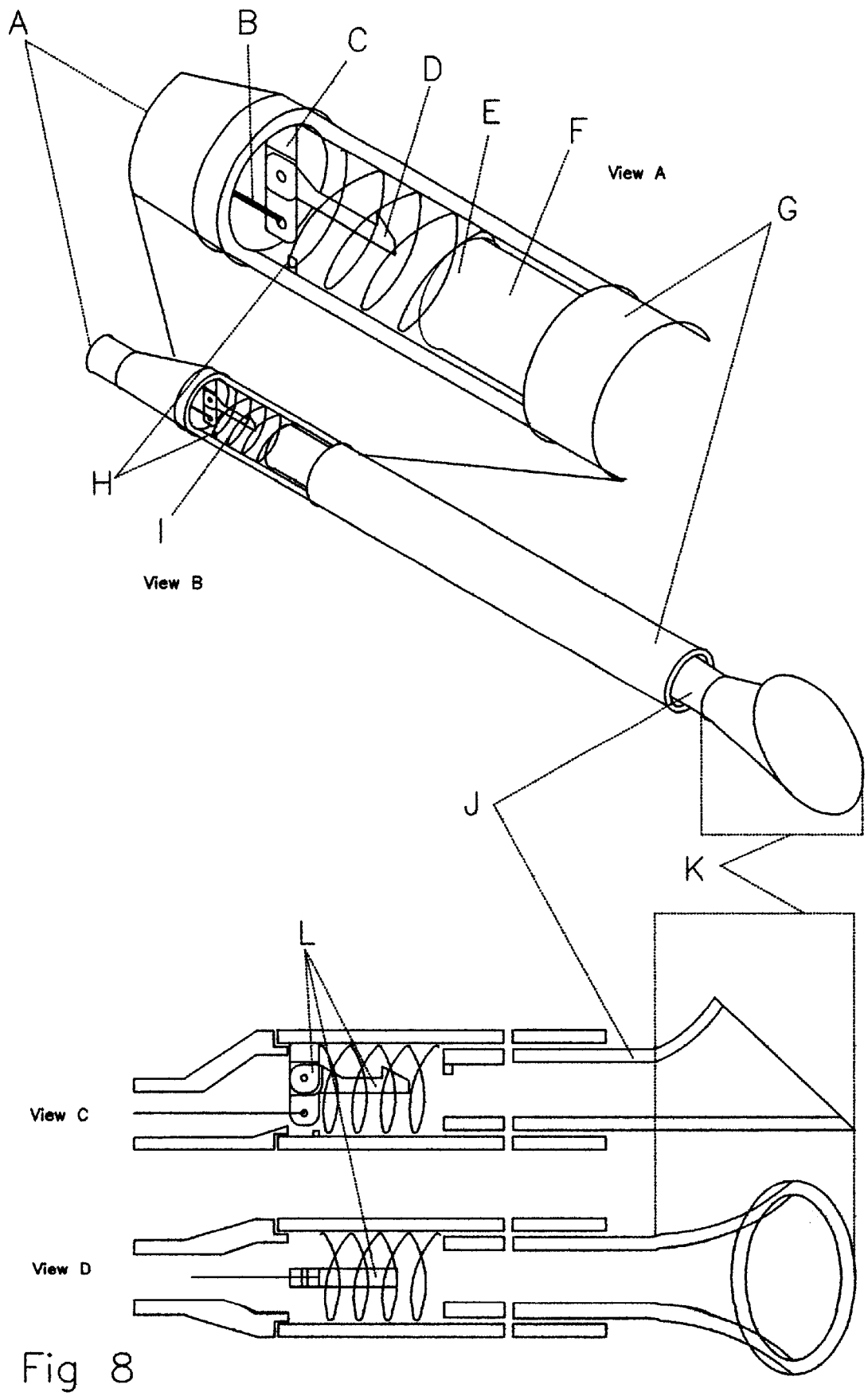

FIG. 8 is a model of the effector and composed of 2 three dimensional views and 2 sectional views of an effector. In the three dimensional views the effector is seen not fixed to the colonoscope tip. The locking system is better visualized in higher magnification of the exposed proximal portion of the effector. In addition the action of the coil spring and the alliance of the external and internal tube is better depicted.

The lables of this drawing are:
A—External tube proximal portion
B—Connecting wire
C—Locking system basement
D—Locking system moving part
E—Groove for ring washer
F—Internal tube
G—External tube
H—Coil spring limiting pin
I—Coil spring
J—Internal tube shaft
K—Internal tube tip
L—Groove for ring washer
M—Coil spring
N—Locking system
O—Connecting wire
P—External tube Drawing Sheet 4

Figure 9:
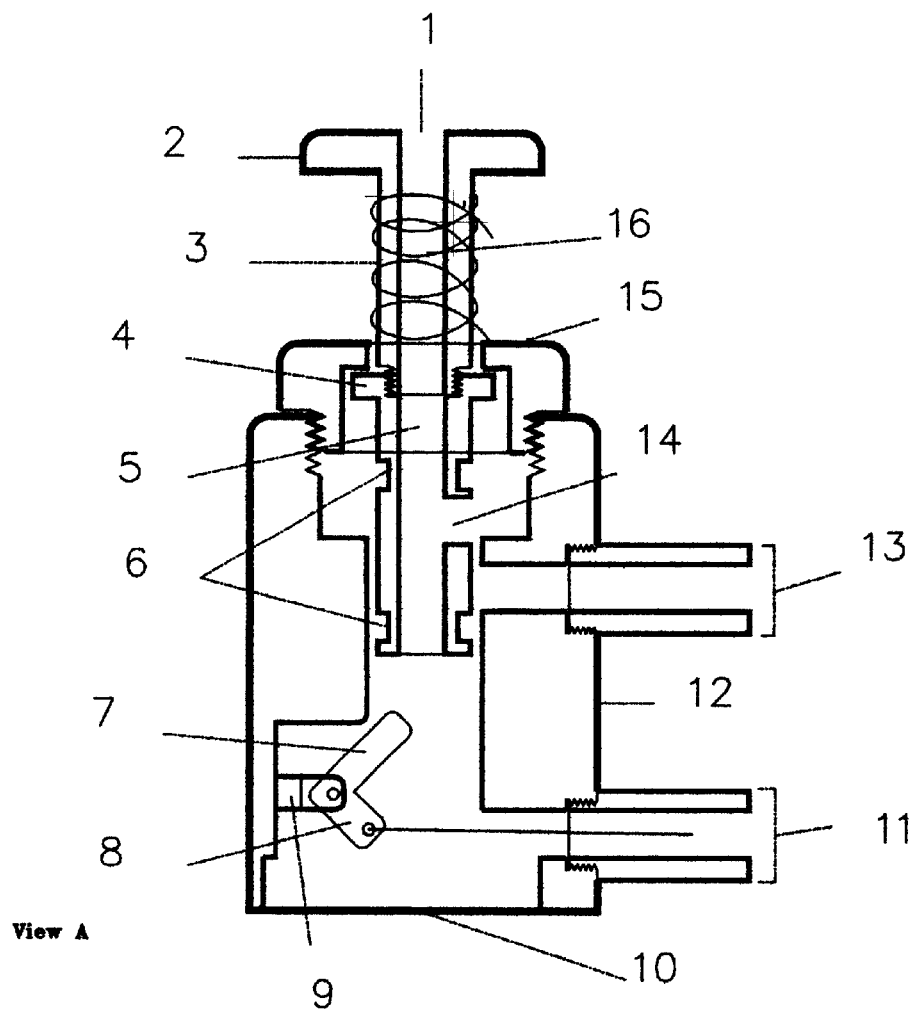
Figure 9:
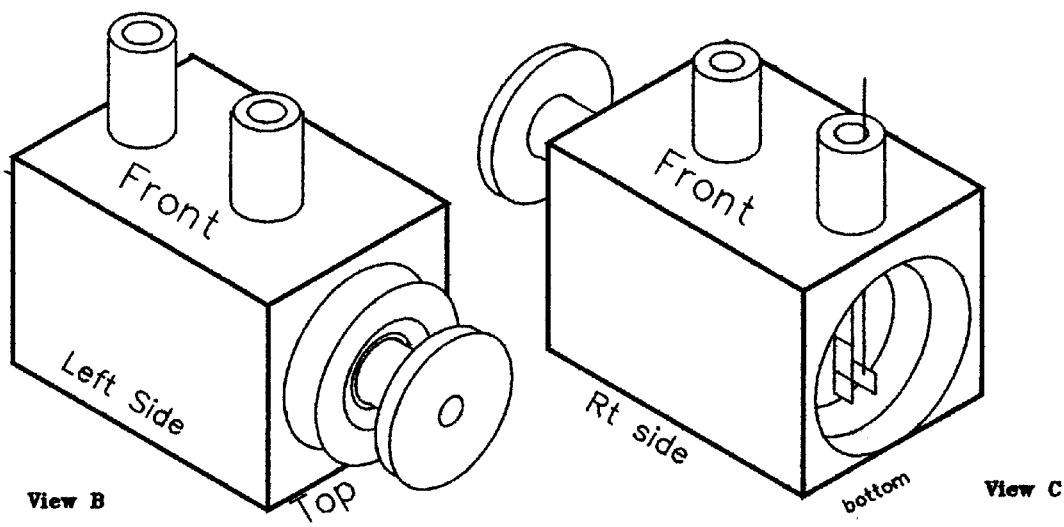

FIG. 9 shows a cross section of the effector and depict the sizes of the several portion of this segment. The sizes are in milimeters.

Drawing Sheet 5

Figure 10:
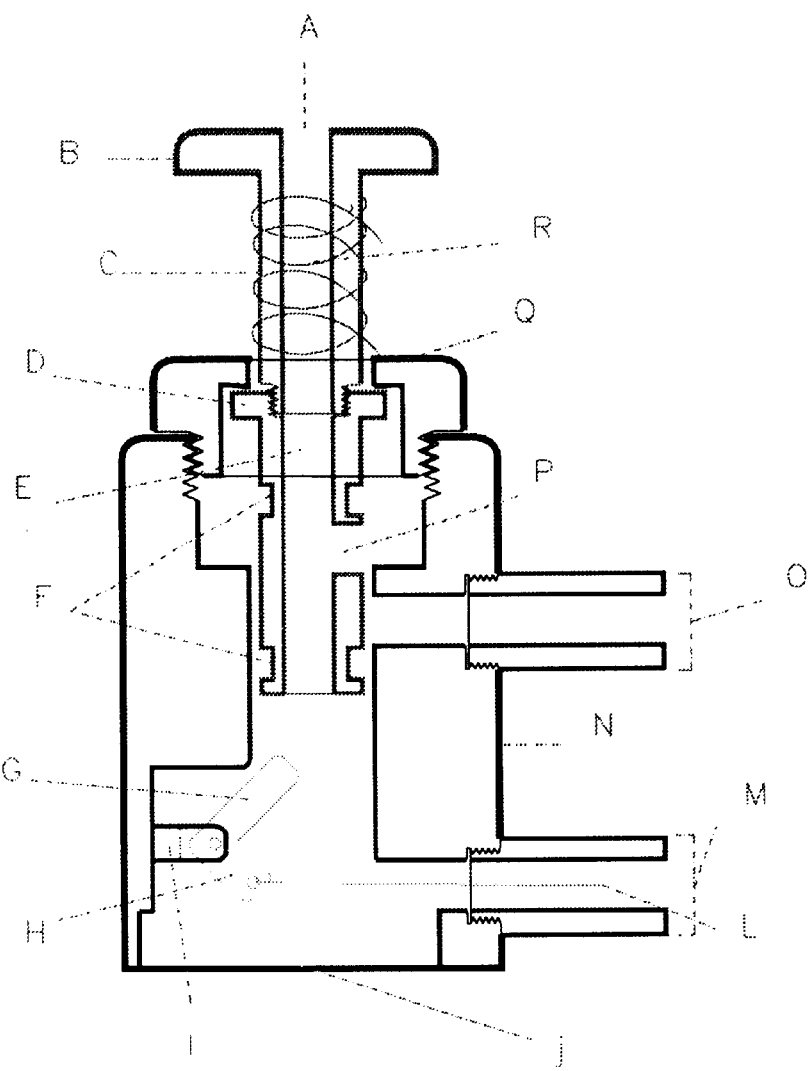
Figure 10:
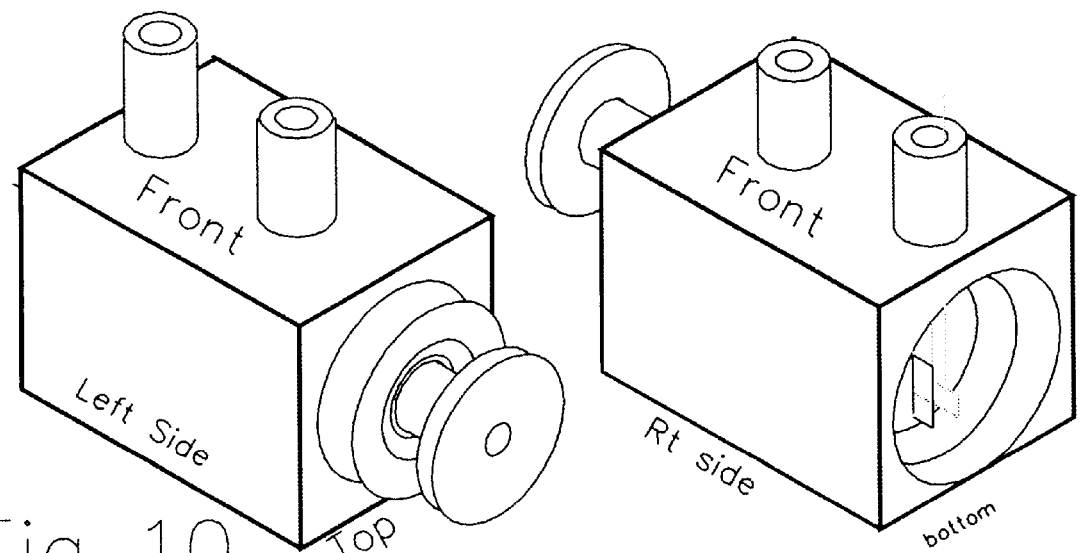

FIG. 10 is a model of controler and composed of 2 three dimensional views of the controler and a sectional view. In sectional view which depict the midline longitudinal section of the controler, the portions of the controler is tabled and the position of the button and button pipe is shown inside the body of the controler. The releasing lever is seen in the chamber of the controler with a connecting wire attached to its short arm. The three dimensional views shows the controler from top and bottom. These view shows the alliance of the button, button pipe, top cover of the body and the position of the front tubes on the body. In the bottom view the bottom surface of the body is exposed for visualization of the inside of the chamber.

The lables of this drawing are:
A—Centeral hole
B—Button
C—Button pipe neck
D—Button pipe limiting edge
E—Button pipe centeral canal
F—Button pipe washer groove
G—Releasing lever long arm
H—Releasing lever short arm
I—Releasing lever basement
J—Body, Base
K—Nothing
L—Connecting wire
M—Connecting tube
N—Body, side
O—Sucction tube
P—Button pipe side hole
Q—Body, top
R—Button pipe coil spring

DETAILED DESCRIPTION OF THE INVENTION

Structural Description

Creeping colonoscope is made up of adding two similar sets of devices to conventional colonoscope; each of them composed of three components. The first component is the effector that would be mounted on the tip of colonoscope. The second part is the controlling component that would be mounted on the control Knob. These two parts are connected to each other by the connecting component. To represent them better, each part is described separately.

1) The Effectors: As it is depicted in FIGS. 7, 8 & 9 (Drawing sheet 2, 3 & 4), the effectors are two similar, mirror imaged pieces on each side of the colonoscope (left & right pieces). Each piece consists of several components.

A—Internal tube: Internal tube or sucking arm is cylindrical in shape. It is placed in the external tube and it is able to be protruded from the external tube it the lumen of the bowel and adheres to the mucosa by the sucking pad on its tip. Adhesion to the mucosa by the vacuum power, the internal tube withdraws in to the external tube. It is composed of two portions:

I—sucking pad: this portion is made of a funnel shaped tube that would be able to increase the area of adherence of the tip of the internal tube to the mucosa. This portion makes an obtuse angle with the tip of the colonoscope to maintain the luminal view of the colonoscope while the tube is attached to the bowel mucosa.

II—Shaft: The shaft of the internal tube is a hollow cylinder that has an external diameter of 4 and internal diameter of 3 millimeters. The proximal portion of the shaft accommodates a groove that contains a ring like washer to seal the internal tube inside the external tube. There is also a small edge at the end of this portion that could be applied to the locking system to lock in place.

B—External tube: This tube is situated along the tip of the colonoscope and is secured to the colonoscope tip (and the contralateral external tube) by two holding strips that are applied to the proximal and distal ends of this tube. The tube contain the internal tube and the internal tube locking system. The internal tube can be moved in and out from the distal end of the external tube. The external diameter of the external tube is 5 mm and the internal diameter of the tube is 4.1 millimeters. At the proximal end of the external tube the diameter of the tube decreases to 2.5 millimeters. The connecting tube adjoins the proximal end of the external tube and the connecting wire passes through this end to reach the locking system.

C—Internal tube locking system: This system is situated near the proximal end of the external tube. The locking system is composed of a fixed base and a moving part and it's small spring. The connecting wire pulls the moving part and this releases the locking system. Releasing the locking system allows the internal tube to be protruded in to the bowel lumen.

2) Connecting components: Controllers and effectors are connected to each other by separate connecting components. Also the suction device is connected to the controller by a tube. The details of the connecting parts are listed below:

A—Connecting tube: This tube is a flexible thin walled tube that connects the controller to the proximal end of the external tube. The diameter of this tube is 3 millimeters and transmits the negative pressure of the suction device in to the effector. This tube also transmits the connecting wire through its lumen.

B—Connecting wire: This wire is a single stranded metal wire that is transmitted through the connecting tube from controller to the effector. This wire is able to move easily in the connecting tube and transfers the releasing command (pulling force) of the releasing lever (inside the controller) in to the locking system (inside the effector).

C—Suction tube: This tube is similar to the connecting tube but does not contain any wire. It connects the suction device to the controller. The tube transmits the negative pressure (vacuum power) of the suction device to the body of the controller. This negative pressure can be transferred to the connecting tube by the valve action of the controller.

3) Controllers: There are two controllers that are mounted over of the control Knob of the colonoscope. These components regulate the operation of the effectors through the connecting components. As it is shown in FIG. 10 each controller composed of several parts.

A—Body: This part is cubical in shape with sides that measure 15 millimeters. The posterior wall (base) of this cube is fixed over the control Knob. The controlling button is situated on the anterior wall (top) of the cube, above the button pipe. The anterior wall contains a metallic cover that is screwed to the body and contains a central opening that allows the passing of the button pipe inside the controller body. There is a coil spring between this cover and the button to hold the button and button pipe in its outermost position. In addition this cover contains a wire spring that can catches in to a transverse groove on the button pipe to secure the position of the button pipe in its middle position (active phase). The appliance of the spring wire to the groove can be felt as a click that indicates the correct position of the button pipe in this position. There is a cylindrical chamber inside the body that is occupied by the button pipe. Two tubes protrude from the inferior wall, that adjoin the connecting tube and the suction tube. These tubes open in to the chamber through two separate openings. The movement of the button pipe inside the chamber that is brought about by pushing of the button, connects the suction tube opening to the opening of the connecting tube inside the chamber. This regulates the transmission of negative pressure of the suction device in to the effector through the connecting tube.

A fixed basement for the releasing lever is situated inside the chamber, near the base on the superior wall. The releasing lever moves on this basement by pushing the button pipe.

B—Releasing lever: This moving part is situated on a fixed basement on superior wall, inside the chamber and can rotate freely on its basement. This part is L shaped and has a long and a short arm. The axis of rotation is at the junction of these two arms. The short arm adjoins the connecting wire and the long arm can be pressed by the button pipe. The pushing force of the button pipe is converted in to the pulling force that can be transmitted via the connecting wire in to the locking system.

Button and button pipe: The button is composed of a circular metallic surface that can be pushed by the finger and attaches from below to a slender cylindrical base called the button pipe. The button pipe consists of a hollow tube that composed of joining of two separate tubes, screwed to each other and share a common central passage called the button pipe canal. At the joining site, there is an edge that limits the excessive inward and outward movement of the button pipe inside the body.

The button surface contains a central opening that opens in to one end of the button pipe canal. This opening would connect the button pipe canal to the atmospheric pressure if it were not blocked by the finger. The button pipe canal has one side hole. This is located in the middle portion of the button pipe. The other end of the button pipe is opened in the inside chamber of the body. When the button is pushed inside, the side hole of the button pipe is positioned in front of the opening of the suction tube, inside the chamber, at the time of active phase of the controller's operation. At this time the negative pressure of the suction device flows through the suction tube, the suction tube opening inside the chamber, the side hole of the button pipe, the central canal of the button pipe, the end hole of the button pipe, the connecting tube opening inside the chamber and the connecting tube, to reach the effector.

Two ring washers that are present above and below the side hole, over the button pipe seal the button pipe inside the chamber. There is a circular groove on the upper portion of the button pipe that can be caught by a wire spring on the top cover of the body. This groove and wire spring stabilizes the movement of the button pipe inside the body in its middle position (active phase). The appliance of the spring wire to the groove can be felt as a click that indicates the correct position of the button pipe. The coil spring between the button and the top cover keep the button and the button pipe in its outward position (inactive phase).

The distal end of the button pipe is able to press the long arm of the releasing lever at the end of its inward movement in the body chamber that result in the rotation of the releasing lever and pulling of the connecting wire (ejection phase).

Functional Description

The creeping colonoscope is composed of several components that operate in concert to move the fiberoptic colonoscope forward. Apparently the function of each component of the instrument should be precisely matched with the other components to obtain a harmonic performance. To represent the functional aspects of this instrument better, the function of each component is described separately.

1) Effectors: Five distinct functional phases can be identified in each effector.

1) Resting phase (phase I): At this stage, the internal tube resides in the external tube (locked in place). No negative pressure is applied to the effector at this stage. The effector does not affect (or disturb) the movement of the colonoscope.

2) Ejection phase (phase II): At this stage, the locking system is released by the pulling of the connecting wire. This results in ejection of the internal tube in to the bowel lumen by the force of the coiled spring inside the external tube.

3) Adhesion phase (phase III): At this stage, the negative pressure is applied to the internal tube via the connecting tube. At this time the internal tube that has been protruded in to the bowel lumen sucks the intraluminal air. Sucking the intraluminal air decreases the intestinal volume and diameter that lead to inward movement of the intestinal walls until the mucosa adhere to the suction pad of the internal tube and blocks its conduit.

4) Retraction phase (Phase IV): Blocking the airflow at the tip of the internal tube by the adherent mucosa raises the negative pressure inside the internal tube. Because the internal tube and external tube act as a closed system due to the sealing effect of the ring washer, the negative pressure rises in both the internal and external tubes and this results in withdrawal of the internal tube inside the external tube. This syringe like action of the internal and external tube withdraws the mucosa toward the colonoscope and therefore moves the colonoscope on ward. It also recoils the released spring inside the external tube. At the end of this phase the internal tube reaches to its previous position and the locking system is applied. Accordingly the internal tube is locked in place and it prevents protruding of the internal tube in to the bowel lumen.

5) Maintenance phase (phase V): At this stage, The internal tube is locked in place but the mucosa is still adhered to the suction pad due to the continuing of the negative pressure. This prevents reverting of the mucosa to the previous position. This phase is continued till the negative pressure is applied to the effector. When the negative pressure is discontinued, the adhered mucosa separates from the sucking pad and the functional cycle of the effector is completed. Completing the fifth phase, the effector enters to the first phase again.

Coordination of the effectors: It should be noted that each of the effectors (left & right) is able to operate independently, but coordination of the effectors is the mainstay aspect of the effectors' performance. Passing straight portions or early flexures of the colon, There is no need for the pulling force of the effectors and the effectors are situated in resting phase (phase I). At this stage as it was mentioned above, the effectors do not affect the colonoscope's forward movement and the colonoscope will move forward only by the pushing force.

Passing more bends and flexures, the pulling forces might become necessary and the effectors can be brought in action. At this time, one of the effectors (for example right) is released and the right effector rushes into the ejection phase (phase II). Entering ejection phase, the internal tube will be protruded in to the bowel lumen and the third phase ensues for the right effector. The mucosa adheres to the protruded internal tube (adhesion phase) and the attached mucosa is pulled toward the colonoscope (retraction phase). At the completion of the Backward movement of the mucosa or forward movement of the colonoscope at the fourth phase, the mucosa remains attached to the sucking pad during maintenance phase (phase V). During all these stages, the left effector remains in the resting phase and when the right effector reaches the maintenance phase the left one may be released. The left effector rushes into phase II and III (ejection & adhesion) sequentially. After adhesion of the left internal tube to the mucosa, the right effector is able to complete its functional cycle and the internal tube can be detached from the mucosa to bring the right effector into phase I. At this time, the left effector is carrying out its functional cycle by going through phase IV (retraction phase) to reach the maintenance phase. At the time, the resting right effector would initiate another functional cycle. These functional cycles are repeated sequentially for the left and right effector until there is no more need for pulling forces of the effectors. At this time both effectors are brought into the resting phase.

It should be noted that during the effector's action, the effector would not release the mucosa unless the other effector has already been adhered to the mucosa. Successive adhesion of the effectors to the mucosa will not permit the retracted mucosa to revert to its previous position. With initial attempts of adhesion and retraction of the effectors, only the mucosa moves toward the colonoscope. This is because that flexible colonic mucosa moves much easier than the colonoscope. As the functional cycles are repeated the colon stretches over the colonoscope up to the point, where the force needed to move the mucosa becomes equal or greater than the force that is needed to move the colonoscope. At this time repeating the functional cycles can move the colonoscope forward.

2) Controller: Three distinct functional phases can be recognized in each controller that correspond to the five phases mentioned in the effectors.

1) Inactive phase (Phase I): This phase corresponds to the resting phase of the effector. During this phase the button is not touched by the finger. The button and button pipe are in their outermost position. At this position the button pipe does not allow the negative pressure of the suction device to be transmitted to the effector. The button pipe is not sealed in the central opening of the body's top cover and the air is able to flow down the gap between them. This prevents the negative pressure rising when it is not connected to the effector.

2) Releasing phase (phase II): This phase coincides with the ejection phase of the effector. In this phase the button is pushed down completely by the finger. The button and button pipe are in the innermost position in the body and the button pipe pushes the releasing lever downward. Pushing down the long arm of the releasing lever, rotates it (by its axis situated midway between the long and short arm) and results in the pulling of the connecting wire adjoined to the short arm. At this point the negative pressure has not yet been transmitted to the effector.

3) Active phase (phase III): This phase coincides to the adhesion, retraction and maintenance phases of the effector. The button is held by the finger in the midway position inside the body. This position is stabilized by the spring wire in the top cover of the body catches the groove upon the button pipe. The appliance of the spring wire to the groove can be felt as a click that indicates the correct position of the button pipe at the time of phase II. At this point the side hole of the button pipe is exactly placed in front of the suction tube opening, thence the negative pressure can be transmitted through the central canal to the effector via the connecting tube.

The releasing lever is no longer pressed by the button pipe at this stage and it returns to its previous position by recoiling of the releasing lever spring.

The adhesion, retraction and maintenance phases of the effector are executed spontaneously and sequentially by applying negative pressure to the effector. The maintenance phase of the effector is continued till the controller is in the active phase. Releasing the button at the end of the active phase terminates this phase by returning the button and the button pipe to the initial position by recoiling the coil spring beneath the button. At this time the controller enters the inactive phase to prepare for the next functional cycle.

Coordination of the controllers: When there is no need for the pulling forces of the effectors, both of the controllers are in inactive phase. When the pulling forces become necessary, one of the controllers (for example right) is brought in to action by pushing the button completely. At this time the right controller enters phase II (releasing phase) and shortly thereafter the button is partially released up to midway where a click can be felt. At this time the right controller enters the active phase. The finger should retain this position till the adhesion and retraction phases take place in the right effector and this effector enters the maintenance phase. At this stage the left controller is brought in to action as explained above for the right controller. On adhering the left effector to the mucosa, the right controller's button can be fully released (and the right effector can be detached). When the left effector reaches the maintenance phase, the right controller's button can be pushed again and the functional cycle can be repeated until there is no need for the pulling force.

Having described the specification for the new colonoscope design, I submit the following as my claims:

1. A colonoscope designed to move into the intestine, comprising:
   a pair of effectors, one on each side of a distal end of the colonoscope, each effector comprising an external tube fixed to a sidewall of the distal end of the colonoscope and an internal tube axially movable within the external tube, a distal end of the internal tube comprising a sucking pad;
   a connecting system for communicating a source of vacuum power to the pair of effectors;
   an ejection system for ejecting the internal tubes forwardly from a retracted position within the external tubes; and
   a control system for regulating movement of the effectors by selectively triggering the ejection system of either effector to eject the internal tube forwardly from the retracted position and selectively applying the vacuum power to either effector to adhere the sucking pad of the internal tube to the bowel mucosa and retract the internal tube thereafter to the retracted position, thereby moving the distal end of the colonoscope relative the intestine.

2. The colonoscope of claim 1 wherein the sucking pad is funnel-shaped.

3. The colonoscope of claim 1 wherein the sucking pad is cut at an angle with respect to the length of the internal tube.

4. The colonoscope of claim 1 wherein the external tubes are secured to the distal end of the colonoscope by holding strips.

5. The colonoscope of claim 1 wherein the ejection system for each effector comprises a locking system for releasably locking the internal tube in the retracted position a spring within the external tube for ejecting the internal tube upon release of the locking system.

6. The colonoscope of claim 5 wherein the control system includes a connecting wire for releasing the locking system for each effector.

7. The colonoscope of claim 6 wherein the connecting system comprises a connecting tube for communicating the vacuum power from the source to each effector.

8. The colonoscope of claim 7 wherein the connecting wire runs inside the connecting tube.

9. The colonoscope of claim 7 wherein the control system comprises a control button for controlling the application of vacuum power to each effector.

10. The colonoscope of claim 9 wherein the control button has a pipe canal which communicates the vacuum power to the atmosphere unless blocked by the user.

11. The colonoscope of claim 9 wherein the control button is also used to release the locking system.

12. The colonoscope of claim 9 wherein the control button is biased to an inactive position where no vacuum power is applied to the effector.

13. A method of advancing an endoscope within a body cavity, comprising:
   a) equipping the endoscope with the following:
      a pair of effectors, one on each side of a distal end of the endoscope, each effector comprising an external tube fixed to a sidewall of the distal end of the endoscope and an internal tube axially movable within the external tube, a distal end of the internal tube comprising a sucking pad;
      a connecting system for communicating vacuum power to the pair of effectors;
      an ejection system for ejecting the internal tubes forwardly from a retracted position within the external tubes; and
      a control system for selectively triggering the ejection system of either effector and selectively applying the vacuum power to either effector;
   b) selectively triggering the ejection system of one effector to eject the internal tube forwardly from the retracted position;
   c) selectively applying the vacuum power said one effector to adhere the sucking pad of the internal tube to a wall of the body cavity and retract the internal tube thereafter to the retracted position, thereby moving the distal end of the endoscope relative the cavity;

d) selectively releasing the vacuum power from said one effector to release it from the body cavity wall e) repeating steps b–d alternately with the other effector.

14. The method of claim 13 wherein the ejection system of the other effector is triggered after the one effector has been retracted but before the one effector is released from the body cavity wall.

15. The method of claim 13 wherein the body cavity is the one of the large intestine and the small intestine and the body cavity wall is the bowel mucosa.

16. The method of claim 13 wherein the ejection system for each effector comprises a locking system for releasably locking the internal tube in the retracted position a spring within the external tube for ejecting the internal tube upon release of the locking system.

17. The method of claim 16 wherein the control system includes a connecting wire for releasing the locking system for each effector.

18. The method of claim 17 wherein the connecting system comprises a connecting tube for communicating the vacuum power from the source to each effector.

19. A The method of claim 17 wherein the control system comprises a control button for controlling the application of vacuum power to each effector.

20. The method of claim 19 wherein the control button is also used to release the locking system.

* * * * *

UNITED STATES PATENT AND TRADEMARK OFFICE
CERTIFICATE OF CORRECTION

PATENT NO.    : 6,309,346 B1
DATED         : October 30, 2001
INVENTOR(S)   : Ashkan Farhadi It is certified that error appears in the above-identified patent and that said Letters Patent is hereby corrected as shown below:

<u>Title page,</u>
Item [76], Inventors, please correct to read:
-- Inventors:    Farhadi; Ashkan
                 300 S. Maple Ave, Apt D-5,
                 Oak Park, IL, 60302, USA Signed and Sealed this Thirteenth Day of August, 2002

*Attest:*

*Attesting Officer*

JAMES E. ROGAN
*Director of the United States Patent and Trademark Office*